US00PP20657P2

(12) United States Plant Patent
Koning

(10) Patent No.: US PP20,657 P2
(45) Date of Patent: Jan. 19, 2010

(54) LAVENDER PLANT NAMED 'BLUE ROYALTY'

(50) Latin Name: *Lavandula angustifolia*
Varietal Denomination: Blue Royalty

(75) Inventor: Lammert Koning, Nuis (NL)

(73) Assignee: Koning Smit Holding B.V., Curacao (AN)

( * ) Notice: Subject to any disclaimer, the term of this patent is extended or adjusted under 35 U.S.C. 154(b) by 0 days.

(21) Appl. No.: 12/228,286

(22) Filed: Aug. 11, 2008

(51) Int. Cl.
*A01H 5/00* (2006.01)

(52) U.S. Cl. ..... Plt./445

(58) Field of Classification Search ..... Plt./445, Plt./226
See application file for complete search history.

(56) References Cited

OTHER PUBLICATIONS

Upov-rom GTITM Plant Variety Database 2009/02, GTI Jouve Retrieval Software, Citation for *Lavandula* 'Blue Royalty', one page.*

* cited by examiner

*Primary Examiner*—June Hwu
(74) *Attorney, Agent, or Firm*—C. A. Whealy

(57) ABSTRACT

A new and distinct cultivar of Lavender plant named 'Blue Royalty', characterized by its compact, upright and somewhat outwardly spreading plant habit; freely branching growth habit; durable green-colored leaves; freely flowering habit; large dark purple-colored flowers positioned on long and strong peduncles; and good garden performance.

2 Drawing Sheets

Botanical designation: *Lavandula angustifolia.*
Cultivar denomination: 'Blue Royalty'.

CROSS-REFERENCED TO CLOSELY RELATED APPLICATIONS

Title: Lavender Plant Named 'Silver Royalty'.
Applicant: Lammert Koning.
Filed: Concurrently with this application (U.S. Plant patent application Ser. No. 12/228,285).

BACKGROUND OF THE INVENTION

The present invention relates to a new and distinct cultivar of Lavender plant, botanically known as *Lavandula angustifolia,* and hereinafter referred to by the name 'Blue Royalty'.

The new Lavender plant is a product of a planned breeding program conducted by the Inventor in Nuis, The Netherlands. The objective of the breeding program was to develop new strong Lavender cultivars with attractive plant form and flower coloration.

The new Lavender plant originated from a cross-pollination made by the Inventor in July, 2004 of a proprietary selection of *Lavandula angustifolia* identified as code number 1755, not patented, as the female, or seed, parent with *Lavandula angustifolia* 'Hidcote', not patented, as the male, or pollen, parent. The new Lavender plant was discovered and selected by the Inventor in August, 2005 as a single flowering plant within the progeny of the stated cross-pollination in a controlled outdoor nursery environment in Nuis, The Netherlands.

Asexual reproduction of the new Lavender by terminal cuttings in a controlled greenhouse environment in Sappemeer, The Netherlands since November, 2005, has shown that the unique features of this new Lavender plant are stable and reproduced true to type in successive generations.

SUMMARY OF THE INVENTION

Plants of the new Lavender have not been observed under all possible environmental conditions. The phenotype may vary somewhat with variations in environment such as temperature and light intensity, without, however, any variance in genotype.

The following traits have been repeatedly observed and are determined to be the unique characteristics of the new Lavender plant. These characteristics in combination distinguish 'Blue Royalty' as a new and distinct cultivar of Lavender:

1. Compact, upright and somewhat outwardly spreading plant habit.
2. Freely branching growth habit.
3. Durable green-colored leaves.
4. Freely flowering habit.
5. Large dark purple-colored flowers positioned on long and strong peduncles.
6. Good garden performance.

Plants of the new Lavender differ from plants of the female parent selection in the following characteristics:

1. Plants of the new Lavender have shorter lateral branches than plants of the female parent selection.
2. Plants of the new Lavender and the female parent selection differ in leaf color.
3. Plants of the new Lavender have thicker peduncles than plants of the female parent selection.

Plants of the new Lavender differ from plants of the male parent, 'Hidcote', in the following characteristics:

1. Plants of the new Lavender are more freely branching than plants of 'Hidcote'.
2. Plants of the new Lavender have larger leaves than plants of 'Hidcote'.
3. Plants of the new Lavender have larger flowers than plants of 'Hidcote'.

4. Plants of the new Lavender are more freely flowering and flower for a longer period of time than plants of 'Hidcote'.

Plants of the new Lavender can be compared to plants of *Lavandula lannatum×Lavandula angustifolia* 'Silver Royalty', disclosed in a U.S. Plant Patent application filed concurrently. Plants of the new Lavender differ from plants of 'Silver Royalty' in the following characteristics:

1. Plants of the new Lavender and 'Silver Royalty' differ in leaf color as plants of 'Silver Royalty' have greyed green-colored leaves.
2. Plants of the new Lavender and 'Silver Royalty' differ in flower color as plants of 'Silver Royalty' have dark blue-colored flowers.

Plants of the new Lavender can also be compared to plants of *Lavandula angustifolia* 'Buena Vista', not patented. Plants of the new Lavender differ from plants of 'Buena Vista' in the following characteristics:

1. Plants of the new Lavender and 'Buena Vista' differ in leaf color as plants of 'Buena Vista' have greyed green-colored leaves.
2. Plants of the new Lavender are more freely flowering than plants of 'Buena Vista'.

BRIEF DESCRIPTION OF THE PHOTOGRAPHS

The accompanying photographs illustrate the overall appearance of the new Lavender plant. These photographs show the colors as true as it is reasonably possible to obtain in colored reproductions of this type. Colors in the photographs may differ slightly from the color values cited in the detailed botanical description which accurately describe the colors of the new Lavender.

The photograph on the first sheet comprises a side perspective view of a typical flowering plant of 'Blue Royalty' grown in a container.

The photograph at the top of the second sheet is a close-up view of a typical inflorescence of 'Blue Royalty'.

The photograph at the bottom of the second sheet is a close-up view of the upper surface of a typical leaf of 'Blue Royalty'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown in 14-cm containers in Paterswolde, The Netherlands during the spring in an outdoor nursery and under conditions and practices which approximate those generally used in commercial Lavender production. Measurements and numerical values represent averages for typical flowering plants. Plants were pinched once and were one year old when the photographs and description were taken. During the production of the plants, day temperatures ranged from 4° C. to 20° C. and night temperatures ranged from 0° C. to 14° C.

Botanical classification: *Lavandula angustifolia* 'Blue Royalty'.

Parentage:

*Female, or seed, parent.*—Proprietary selection of *Lavandula angustifolia* identified as code number 1755, not patented.

*Male, or pollen, parent.*—*Lavandula angustifolia* 'Hidcote', not patented.

Propagation:

*Type.*—Terminal vegetative cuttings.

*Time to initiate roots, summer.*—About two weeks at 14° C. to 25° C.

*Time to initiate roots, winter.*—About three weeks at 14° C. to 25° C.

*Time to produce a rooted young plant, summer.*—About eight weeks at 14° C. to 25° C.

*Time to produce a rooted young plant, winter.*—About ten weeks at 14° C. to 25° C.

*Root description.*—Fine, fibrous; white in color.

*Rooting habit.*—Freely branching; dense.

Plant description:

*Form.*—Herbaceous perennial subshrub. Compact, upright and outwardly spreading plant habit; broad inverted triangle.

*Growth habit.*—Moderately vigorous.

*Branching habit.*—Freely branching habit, about 46 lateral branches.

*Plant height.*—About 36.5 cm.

*Plant width.*—About 38.2 cm.

*Lateral branch description.*—Length: About 12.5 cm. Diameter: About 2 mm. Internode length: About 2.2 cm. Strength: Strong. Aspect: Mostly upright to outward. Texture: Pubescent. Color: Close to 137C; pubescence, close to 192D.

*Foliage description.*—Arrangement: Opposite, simple; sessile. Length: About 3.9 cm. Width: About 4 mm. Shape: Lanceolate. Apex: Broadly acute. Base: Cuneate. Margin: Entire. Texture, upper and lower surfaces: Sparsely pubescent. Fragrance: Very aromatic, pungent. Venation pattern: Pinnate. Color: Developing leaves, upper surface: Between 141B and 143A. Developing leaves, lower surface: Close to 137D. Fully expanded leaves, upper surface: Between 137A and 147A; venation, close to 147A; pubescence, close to 192D. Fully expanded leaves, lower surface: Between 137B and 147B; venation, close to 137B; pubescence, close to 192D.

Flower description:

*Flower arrangement and shape.*—Single flowers arranged on long and strong spikes. Freely flowering, about 86 open flowers and flower buds per spike; flowers salverform with a two-lobed upper lip and a three-lobed lower lip.

*Natural flowering season.*—Long flowering period; continuous throughout the summer in The Netherlands.

*Flower longevity on the plant.*—Individual inflorescences last about ten days on the plant. Flowers not persistent.

*Fragrance.*—None detected.

*Flower buds.*—Length: About 6 mm. Diameter: About 2.5 mm. Shape: Ovate. Color: Close to 86A; towards the base, close to 145C.

*Inflorescence size.*—Height: About 4.5 cm. Diameter: About 1.6 cm.

*Flowers.*—Diameter: About 6 mm. Depth (height): About 1 cm.

*Petals.*—Lip length: About 9 mm. Lip width: About 2 mm. Lip shape: Roughly spatulate. Lip: Rounded; emarginate. Lip margin: Entire. Lip texture, upper and lower surfaces: Smooth, glabrous. Lip color: When opening, upper and lower surfaces: Close to 85A; tube, close to N78B; towards the base, close to 155D. Fully opened, upper and lower surfaces: Close to 84A; tube, close to N78B; towards the base, close to 155D. With development, color becoming closer to 86C.

*Sepals.*—Arrangement: Five sepals fused into a campanulate tube. Length: About 6 mm. Width: About 1 mm. Shape: Lanceolate. Apex: Acute. Sepal margin: Entire. Sepal texture, upper and lower surfaces: Pubescent. Color, immature and mature, upper and lower surfaces: Close to 86A; towards the base, close to 145C.

*Peduncles.*—Strength: Strong. Length: About 13.3 cm. Diameter: About 1.5 mm. Aspect: Mostly upright. Texture: Pubescent. Color: Close to 137C; pubescence, close to 192D.

*Pedicels.*—Strength: Moderately strong. Length: About 1 mm. Diameter: About 0.5 mm. Aspect: About 45° from the peduncle. Texture: Pubescent. Color: Close to 145D; pubescence, close to 192D.

*Reproductive organs.*—Stamens: Quantity per flower: Four. Filament length: About 1 mm. Anther shape: Reniform. Anther length: About 0.5 mm. Anther color: Close to 165A. Pollen amount: Scarce. Pollen color: Close to 163A. Pistils: Quantity per flower: One. Pistil length: About 4.5 mm. Stigma shape: Club-shaped. Stigma color: Close to 155A. Style length: About 4 mm. Style color: Close to 155A. Ovary color: Close to 143A.

*Seed/fruit.*—Seed and fruit production has not been observed.

Disease/pest resistance: Plants of the new Lavender have not been noted to be resistant to pathogens and pests common to Lavender.

Garden performance: Plants of the new Lavender have exhibited good tolerance to rain and wind and have been observed to tolerate temperatures from about −15° C. to about 40° C.

It is claimed:

1. A new and distinct Lavender plant named 'Blue Royalty' as illustrated and described.

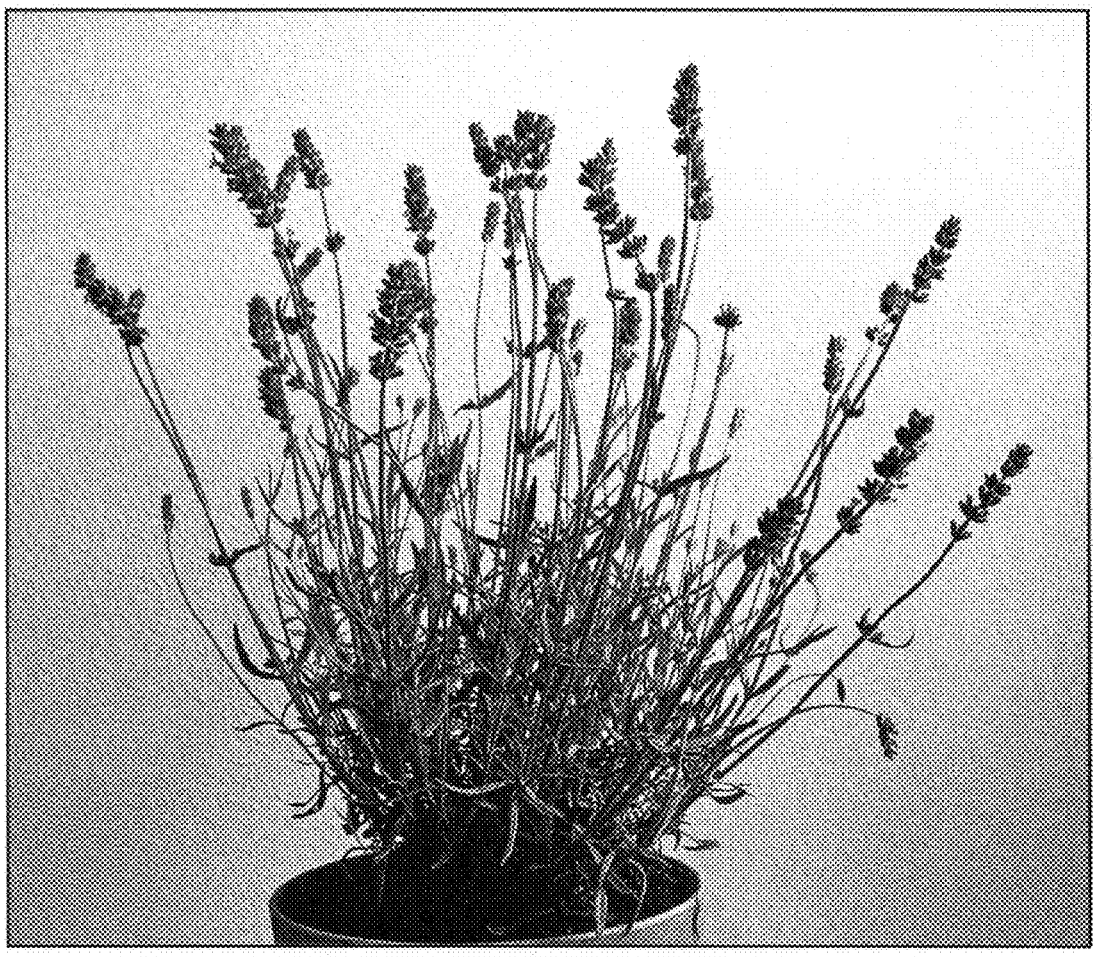

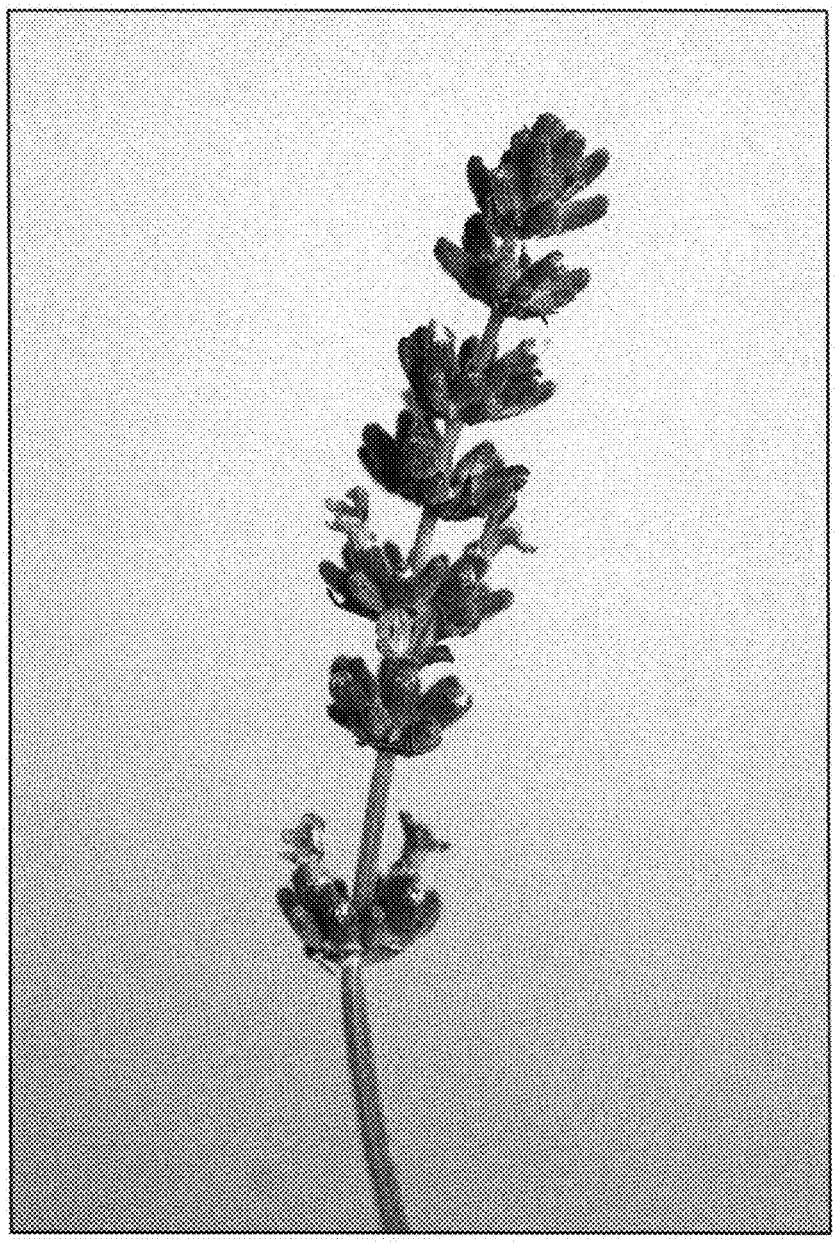
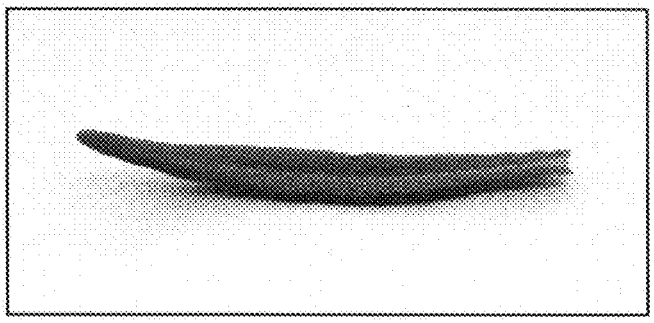

* * * * *